United States Patent
Beeson et al.

(10) Patent No.: US 8,691,247 B2
(45) Date of Patent: Apr. 8, 2014

(54) SKIN REJUVENATION CREAM

(75) Inventors: William H. Beeson, Carmel, IN (US); Alvin T. Rockhill, Akron, OH (US)

(73) Assignee: Ad Lunam Labs Inc., Spearfish, SD (US)

( * ) Notice: Subject to any disclaimer, the term of this patent is extended or adjusted under 35 U.S.C. 154(b) by 145 days.

(21) Appl. No.: 11/957,564

(22) Filed: Dec. 17, 2007

(65) Prior Publication Data

US 2008/0153757 A1 Jun. 26, 2008

Related U.S. Application Data

(60) Provisional application No. 60/877,202, filed on Dec. 26, 2006.

(51) Int. Cl.
*A61K 8/37* (2006.01)
*A61K 8/27* (2006.01)
*A61K 8/35* (2006.01)
*A61K 8/365* (2006.01)
*A61K 8/44* (2006.01)
*A61K 8/67* (2006.01)
*A61K 8/97* (2006.01)
*A61Q 19/08* (2006.01)
*A61K 38/08* (2006.01)
A61K 31/355 (2006.01)
A61K 31/375 (2006.01)
A61K 31/19 (2006.01)
A61K 47/46 (2006.01)
A61K 47/12 (2006.01)
A61K 36/55 (2006.01)

(52) U.S. Cl.
CPC . *A61Q 19/08* (2013.01); *A61K 8/27* (2013.01); *A61K 8/37* (2013.01); *A61K 8/44* (2013.01); *A61K 8/676* (2013.01); *A61K 8/678* (2013.01); A61K 31/355 (2013.01); A61K 31/375 (2013.01); *A61K 38/08* (2013.01); A61K 31/19 (2013.01); A61K 47/46 (2013.01); A61K 47/12 (2013.01); A61K 36/55 (2013.01); A61K 2300/00 (2013.01)
USPC ......... 424/401; 514/18.8; 514/21.8; 514/458; 514/469; 514/474; 514/745

(58) Field of Classification Search
CPC ........... A61Q 19/08; A61K 8/44; A61K 8/27; A61K 8/37; A61K 8/676; A61K 31/355; A61K 8/678; A61K 31/375; A61K 47/46
See application file for complete search history.

(56) References Cited

U.S. PATENT DOCUMENTS

| | | | | |
|---|---|---|---|---|
| 4,938,969 A | * | 7/1990 | Schinitsky et al. | 424/642 |
| 5,256,700 A | | 10/1993 | Aeschbach et al. | 514/732 |
| 5,358,752 A | * | 10/1994 | Evans et al. | 424/450 |
| 5,643,586 A | * | 7/1997 | Perricone | 424/401 |
| 5,851,537 A | * | 12/1998 | Alberts et al. | 424/400 |
| 5,859,293 A | | 1/1999 | Bailey et al. | 562/467 |
| 6,066,327 A | * | 5/2000 | Gubernick et al. | 424/401 |
| 6,180,144 B1 | * | 1/2001 | Hill et al. | 426/3 |
| 6,217,914 B1 | * | 4/2001 | Meisner | 424/642 |
| 7,022,317 B2 | | 4/2006 | Erdelmeier | 424/59 |
| 2003/0039668 A1 | * | 2/2003 | Gulla et al. | 424/401 |
| 2003/0144635 A1 | * | 7/2003 | Connor | 604/294 |
| 2004/0005342 A1 | * | 1/2004 | Bernerd | 424/401 |
| 2006/0045896 A1 | * | 3/2006 | Morariu | 424/401 |
| 2006/0110415 A1 | * | 5/2006 | Gupta | 424/401 |

FOREIGN PATENT DOCUMENTS

| | | | | |
|---|---|---|---|---|
| GB | 2418855 A | | 12/2006 | ............ A61K 47/14 |
| KR | 2003016547 A | * | 3/2003 | |
| WO | WO98/23152 A | | 6/1998 | ............ A01N 43/08 |
| WO | WO00/56327 A | | 9/2000 | ............ A61K 31/195 |

OTHER PUBLICATIONS

Schallreuter et al., Biochemical and Biophysical Research Comminications, 262: 423-428 (1999).*
Robinson et al., International Journal of Cosmetic Science, 27(3): 155-160 (2005) (Abstract).*

* cited by examiner

*Primary Examiner* — Kortney L Klinkel
*Assistant Examiner* — Lisbeth C Robinson
(74) *Attorney, Agent, or Firm* — Alvin T. Rockhill

(57) ABSTRACT

The subject invention relates to a skin cream that can be used to moisturize and rejuvenate skin that has been damaged by exposure to sunlight or which has simply been affected over the years by intrinsic aging. It inhibits the formation of wrinkles and in some cases reduces the depth of existing wrinkles or eliminates them entirely. This invention is based upon the discovery that alkyl lactates, such as ethyl lactate, can be used to improve the penetration of active ingredients in skin care formulations deep into lower layers of the skin tissue. The present invention more specifically discloses a topical formulation comprising ascorbic acid, an amino acid selected from the group consisting of phenylalanine and tyrosine, a non-toxic zinc salt, an alkyl lactate, and a pharmaceutically acceptable carrier.

14 Claims, No Drawings

SKIN REJUVENATION CREAM

This patent application claims benefit of U.S. Provisional Patent Application Ser. No. 60/877,202, filed on Dec. 26, 2006. The teachings of U.S. Provisional Patent Application Ser. No. 60/877,202 are incorporated herein by reference in their entirety.

BACKGROUND OF THE INVENTION

Skin care has been practiced for thousands of years, dating back to the Ancient Egyptians. Cleopatra was known for her skin car regimen, and is said to have discovered some of the first anti-aging methods. Skin care has evolved through the years with every generation being eager to slow, prevent or reverse the aging process.

Countless skin care products are commercially available for beautification of the skin and to fight wrinkle formation. For example, U.S. Pat. No. 4,938,969 discloses a composition for reducing the depth or intensity of fine wrinkles in skin affected by intrinsic or photo-induced aging. The topical formulation described by U.S. Pat. No. 4,938,969 is comprised of ascorbic acid, tyrosine and a non-toxic zinc salt and is preferably formulated in a hydrophilic ointment or cream base. This composition is reported to be effective for the treatment of aging or photo-damaged skin and in reducing wrinkles.

The effectiveness of all skin care products is normally contingent upon delivery of the active ingredients therein through the stratum corneum and viable epidermis into the dermis layer of the skin structure. This is because the active ingredients in the skin care product cannot be effective unless they penetrate through the dead layers of skin tissue and into the dermis layer of living skin cells. This is normally a difficult proposition for water soluble active ingredients, such as ascorbic acid, because the stratum corneum is a good water barrier. The stratum corneum and viable epidermis act to protect the body by holding water therein to prevent dehydration and by keeping external water which is frequently contaminated out of the body.

SUMMARY OF THE INVENTION

The subject invention relates to a skin cream that can be used to rejuvenate skin that has been damaged by exposure to sunlight or which has simply been affected over the years by intrinsic aging. It can also be used to slow the rate of photo-induced aging to maintain beautiful skin tone and texture over the years. It inhibits the formation of wrinkles and in some cases reduces the depth of existing wrinkles or eliminates them entirely. In some cases, the skin cream of this invention also lightens age spots and other types of blemishes associated with aging.

The skin cream of this invention is non-irritating and can be used to soothe the pain of sunburns and in the treatment of red, irritated, dry, cracked or itchy skin. It can also be used in treating atopic dermatitis, psoriasis, and ichthyosis by moisturizing the skin. The skin cream of this invention is typically applied to the face, décolletage, and/or hands of a patient. However, it can be generally used anywhere on the skin of a patient's body. For instance, it can also be applied to the patient's feet, chest, back, legs, ankles, arms, and/or wrists as desired.

This invention is based upon the discovery that alkyl lactates, such as ethyl lactate, can be used to improve the penetration of active ingredients in skin care formulations deep into lower layers of the skin tissue. For instance, ethyl lactate can be included in aqueous based skin creams, such as oil in water emulsions, to deliver active ingredients deep into the skin structure. Ethyl lactate is particularly desirable for utilization in conjunction with skin cream formulations that contain water soluble active ingredients, such as ascorbic acid (Vitamin C). This is beneficial because the overall effectiveness of skin creams that utilize ascorbic acid and/or other water soluble active ingredients is contingent upon delivery of the ascorbic acid through the outer layers of the stratum corneum and viable epidermis and into the dermis layer of the skin structure.

The present invention more specifically discloses a topical formulation comprising about 1 weight percent to about 20 weight percent ascorbic acid, about 1 weight percent to about 10 weight percent of an amino acid selected from the group consisting of phenylalanine and tyrosine, about 0.5 weight percent to about 5 weight percent of a non-toxic zinc salt, about 0.01 weight percent to about 20 weight percent of an alkyl lactate, wherein the alkyl group in the alkyl lactate contains from 2 to about 12 carbon atoms, and a pharmaceutically acceptable carrier.

The subject invention further reveals a topical formulation comprising about 1 weight percent to about 20 weight percent ascorbic acid, about 1 weight percent to about 10 weight percent phenylalanine, about 0.5 weight percent to about 5 weight percent of a non-toxic zinc salt, and a pharmaceutically acceptable carrier.

The present invention also discloses a method of rejuvenating human skin affected by intrinsic aging and/or photo-induced aging, said method comprising topically applying a topical formulation to the skin, wherein the topical formulation is comprised of about 1 weight percent to about 20 weight percent ascorbic acid, about 1 weight percent to about 10 weight percent of an amino acid selected from the group consisting of phenylalanine and tyrosine, about 0.5 weight percent to about 5 weight percent of a non-toxic zinc salt, about 0.01 weight percent to about 20 weight percent of an alkyl lactate, wherein the alkyl group in the alkyl lactate contains from 2 to about 12 carbon atoms, and a pharmaceutically acceptable carrier.

The subject invention further discloses a method of rejuvenating human skin affected by intrinsic aging and/or photo-induced aging, said method comprising topically applying a topical formulation to the skin, wherein the topical formulation is comprised of about 1 weight percent to about 20 weight percent ascorbic acid, about 1 weight percent to about 10 weight percent phenylalanine, about 0.5 weight percent to about 5 weight percent of a non-toxic zinc salt, and a pharmaceutically acceptable carrier.

It is preferred for the alkyl lactate utilized in the topical formulations of this invention to be ethyl lactate with it being more preferred for the alkyl lactate to be a mixture of ethyl lactate and iso-amyl lactate. It is also preferred for the topical formulations of this invention to contain α-tocopherol, carnosic acid, idebenone, and/or palmitoyl pentapeptide.

The present invention also reveals a topical formulation comprising about 0.01 weight percent to about 5 weight percent idebenone, about 0.01 weight percent to about 20 weight percent of an alkyl lactate, wherein the alkyl group in the alkyl lactate contains from 2 to about 12 carbon atoms, and a pharmaceutically acceptable carrier.

The subject invention further discloses a topical formulation comprising (1) about 0.01 weight percent to about 2 weight percent of at least one polyphenolic antioxidant selected from the group consisting of condensed proanthocyanidins, chlorogenic acid, quinic acid, and ferulic acid, (2) about 0.01 weight percent to about 20 weight percent of an alkyl lactate, wherein the alkyl group in the alkyl lactate contains from 2 to about 12 carbon atoms, and (3) a pharmaceutically acceptable carrier.

The present invention also reveals a topical formulation comprising about 0.01 weight percent to about 5 weight percent carnosic acid, about 0.01 weight percent to about 20 weight percent of an alkyl lactate, wherein the alkyl group in the alkyl lactate contains from 2 to about 12 carbon atoms, and a pharmaceutically acceptable carrier.

DETAILED DESCRIPTION OF THE INVENTION

The topical skin cream formulations of this invention will normally contain from about 1 weight percent to about 20 weight percent ascorbic acid (Vitamin C). Higher levels of ascorbic acid can be used, but do not generally yield a better result. However, in cases where the ascorbic acid is utilized at levels of less than about 1 weight percent the improvement of treated skin in minimal. It is typically preferred for the ascorbic acid to be utilized in the topical skin cream formulation at a level which is within the range of about 5 weight percent to about 15 weight percent. It is typically more preferred for the ascorbic acid to be utilized in the topical skin cream formulation at a level which is within the range of about 8 weight percent to about 12 weight percent. For improved long term shelf stability the level of ascorbic acid will typically be limited to an amount which is within the range of 2 weight percent to 5 weight percent and preferably within the range of 3 weight percent to 4.5 weight percent.

The topical skin cream formulations of this invention will also typically contain from about 0.1 weight percent to about 5 weight percent of a non-toxic zinc salt. The skin cream formulation will preferably contain from about 0.5 weight percent to about 4 weight percent of the zinc salt and will most preferably contain from about 1 to about 3 weight percent of the zinc salt. The zinc salt will preferably be a water soluble zinc salt, such as zinc bacitracin (baciferm), zinc salicylate (zinc salt of 2-hydroxybenzoic acid), or zinc sulfate. Zinc sulfate is generally preferred for used as the zinc salt. However, zinc salicylate offers the advantage of providing antiseptic action which can be desirable for preventing the growth of bacteria in the skin cream formulation during storage and can also be beneficial in certain patients, such as patients suffering from acne.

The topical skin cream formulations of this invention will also typically contain from about 1 weight percent to about 10 weight percent of an amino acid selected from the group consisting of phenylalanine and tyrosine. It is normally preferred for the amino acid to be phenylalanine. The skin cream will generally contain from about 2 weight percent to about 8 weight percent of the amino acid and will preferably contain from about 2.5 weight percent to about 4 weight percent of the amino acid.

It is important for the topical skin cream formulations of this invention to contain an alkyl lactate for the active ingredients, particularly the ascorbic acid, to better penetrate through the stratum corneum and the viable epidermis to gain entry into the dermis. This is because the active ingredients of the skin cream can only serve their intended purpose after reaching the living dermis layer of the skin. The alkyl lactate will normally be present in the skin cream formulation at a level which is within the range of about 0.01 weight percent to about 20 weight percent. The alkyl lactate will more typically be present in the skin cream formulation at a level which is within the range of about 0.1 weight percent to about 15 weight percent. The alkyl lactate will preferably be present in the skin cream formulation at a level which is within the range of about 0.2 weight percent to about 1 weight percent and will more preferably be present at a level which is within the range of about 0.2 weight percent to about 0.5 weight percent.

The alkyl lactate utilized will typically have an alkyl group that contains from 2 to about 12 carbon atoms and will accordingly be of the structural formula:

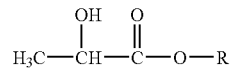

wherein R represents an straight chained or a branched alkyl group that contains from 2 to 12 carbon atoms. It is preferred for the alkyl group to contain from 2 to about 6 carbon atoms. Ethyl lactate is highly preferred because it is highly dispersible in aqueous solutions. Ethyl lactate is of the structural formula:

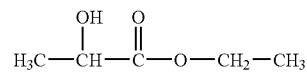

and is a colorless liquid having a strong odor. It is preferred to utilize a mixture of ethyl lactate with a higher molecular weight alkyl lactate in cases where oil soluble active ingredients, such as α-tocopherol are included in the topical skin cream formulation. Isoamyl lactate is preferred for utilization in such mixtures. Isoamyl lactate is of the structural formula:

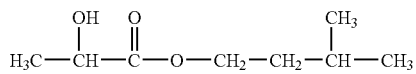

and is a colorless liquid having a pleasant mild odor.

In cases where a mixture of ethyl lactate and isoamyl lactate are utilized in the skin cream formulation the weight ratio of ethyl lactate to isoamyl lactate will typically be within the range of about 1:10 to about 20:1. The weight ratio of ethyl lactate to isoamyl lactate will more typically be within the range of about 1:5 to about 10:1. Such mixtures of ethyl lactate and isoamyl lactate will preferably contain from about 30 weight percent to 70 weight percent ethyl lactate and from about 30 weight percent to about 70 weight percent isoamyl lactate. Such mixtures of ethyl lactate and isoamyl lactate will more preferably contain from about 40 weight percent to 60 weight percent ethyl lactate and from about 40 weight percent to about 60 weight percent isoamyl lactate. Such mixtures of ethyl lactate and isoamyl lactate will most preferably contain from about 45 weight percent to 55 weight percent ethyl lactate and from about 45 weight percent to about 55 weight percent isoamyl lactate.

It is highly desirable for the skin cream formulations of this invention to contain α-tocopherol (Vitamin E) for a number of important reasons. For instance, α-tocopherol is a powerful antioxidant that can serve to protect the skin cells of a patient being treated from photo-induced damage as well as other causes of oxidative aging. The α-tocopherol also helps to preserve the skin cream composition from oxidation during storage. This is particularly important in compositions that contain high levels of ascorbic acid, such as compositions that contain over 3 weight percent and particularly 5 weight percent ascorbic acid. It was also unexpectedly found that α-tocopherol helps to mask the odor of ethyl lactate in the skin cream compositions of this invention. This makes the skin cream much more pleasant for patients to use and is of particular importance in cases where the patient will used the skin cream formulation over a prolonged period of time.

It was found that α-tocopherol helps to prevent the skin cream compositions of this invention from yellowing due to oxidation of the ascorbic acid therein. However, it was unexpectedly found that the α-tocopherol must be present at a specific level to protect ascorbic acid from oxidation and to accordingly prevent the skin cream formulation from yellowing. More specifically, in cases where α-tocopherol is present at levels of less than about 5 weight percent the skin cream is prone of yellowing and in cases where the α-tocopherol is present at levels of greater than about 25 weight percent the skin cream is also prone to yellowing. In such cases, additional antioxidants, such as butylated hydroxytoluene (BHT) should be included in the formulation to prevent oxidation of the ascorbic acid. However, in cases where the α-tocopherol is present at a level which is within the range of about 10 weight percent to about 20 weight percent the skin cream formulations of this invention the ascorbic acid is resistant of oxidative degradation. For this reason, it is preferred to include α-tocopherol at a level which is within the range of about 5 weight percent to about 25 weight percent with it being more preferred to include the α-tocopherol at a level which is within the range of about 10 weight percent to about 20 weight percent. In cases where other agents are used to protect the ascorbic acid from oxidation, α-tocopherol can be beneficially employed in the skin cream at levels which are within the range of 1 weight percent to 30 weight percent. In such cases the α-tocopherol will typically be employed in the skin cream at levels which are within the range of 2 weight percent to 8 weight percent and preferably within the range of 3 weight percent to 5 weight percent. In such formulations it is frequently desirable to include about 0.1 weight percent to about 5 weight percent BHT to further inhibit yellowing. Such formulations will typically contain from about 0.5 weight percent to 2 weight percent BHT and will more typically contain from 0.8 weight percent to 1.2 weight percent BHT.

Carnosic acid can be included in the skin cream formulations of this invention to provide a higher level of protection against photo-induced and other types of oxidative attack on skin cells. The carnosic acid will typically be included in the skin cream formulation at a level which is within the range of 0.01 weight percent to 1.5 weight percent. It is normally preferred to include the carnosic acid at a level which is within the range of 0.05 weight percent to 1 weight percent with levels of 0.1 weight percent to 0.8 weight percent being most preferred. The carnosic acid is naturally found in Libiatae plants, such as rosemary, marjoram, and sage.

U.S. Pat. No. 5,859,293 and U.S. Pat. No. 5,256,700 disclose techniques for extracting high purity carnosic acid from rosemary and sage. For example, U.S. Pat. No. 5,256,700 discloses a process for obtaining carnosic acid comprising extracting a vegetable material selected from the group consisting of sage and rosemary with an apolar solvent to obtain an extract containing apolar compounds including carnosic acid, contacting the extract with an adsorbent material having an affinity for polar compounds for adsorbing the carnosic acid to separate the carnosic acid from the apolar compounds of the extract, desorbing the adsorbent material with a polar solvent to obtain the carnosic acid in the solvent and then evaporating the polar solvent from the carnosic acid to obtain a residue containing the carnosic acid.

Mixtures of ethyl lactate and isoamyl lactate can beneficially be used to extract carnosic acid from Libiatae plants, such as rosemary, marjoram, and sage. For instance, a mixture containing from about 30 weight percent to 70 weight percent ethyl lactate and about 30 weight percent to about 70 weight percent isoamyl lactate can be used to extract carnosic acid from such Libiatae plants. In such a procedure, the mixture of ethyl lactate and isoamyl lactate is mixed with about 30 parts by weight to about 70 parts by weight of water and heated to a temperature which is within the range of about 70° C. to about 100° C. Then ground leaves of the Libiatae plant are mixed into the solution of the ethyl lactate, isoamyl lactate and water. Then the extract of the Libiatae plant is recovered by filtering it from the solid matter, such as leaves and plant material. At this point, the extract from the Libiatae plant can be employed in making the skin creams of this invention. It should be noted that additional ethyl lactate and/or isoamyl lactate can be added at attain the desired levels in the final skin cream.

Some methods for the preparation of carnosic acid by chemical synthesis have also been proposed in the literature by W. L. Meyer et al. [Tetrahedron Letters 1966, 4261; 1968, 2963; J. Org. Chem. 41, 1005 (1976)]. However, the syntheses involved are long and complex and, for economic reasons, cannot be applied to an industrial process. In addition, these syntheses lead to racemic mixtures of carnosic acid precursors and not to the pure enantiomers. It should also be pointed out that these works stop at the preparation of carnosic acid precursors and omit to describe the final preparation step(s). Another method of obtaining carnosic acid has been described in the literature by Brieskorn and Domling [Arch. Pharm. 302, 641 (1969)], comprising the catalytic reduction of carnosol. Once again, the application of this process on a large scale is not be envisaged because carnosol is not readily available on a commercial basis. For these reasons the carnosic acid used in the skin creams formulations of this invention will normally be obtained by extraction from a Libiatae plant, such as rosemary or marjoram. Accordingly, rosemary or marjoram extract will typically be used in the practice of this invention as the source of carnosic acid. However, to reduce the possibility of allergic reactions to the skin cream formulation the skin cream formulation will preferably be free of rosemary, sage, marjoram and other Libiatae plants.

It is preferred for the skin cream formulations of this invention to also contain idebenone. The idebenone will typically be present in the skin cream formulation at a level which is within the range of about 0.01 weight percent to about 5 weight percent. The idebenone will preferably be present in the skin cream formulation at a level which is within the range of about 0.05 weight percent to about 3 weight percent and will more preferably be present at a level which is within the range of about 0.1 weight percent to about 1 weight percent.

Palmitoyl pentapeptide can also be included in the skin cream formulations of this invention. Palmitoyl pentapeptide stimulates human fibroblasts to produce collagen and elastin which fight wrinkle formation and can reduce or eliminate existing wrinkles. However, as with all active ingredients in antiwrinkle creams palmitoyl pentapeptide needs to be delivered deep into the dermis of the skin structure to attain a maximum level of effectiveness. The topical skin cream formulations of this invention accordingly can be used to facilitate the delivery of the palmitoyl pentapeptide deep into the dermis of a patient. The palmitoyl pentapeptide will normally be included at a level which is within the range of about 0.05 weight percent to about 8 weight percent. The palmitoyl pentapeptide will more typically be included at a level which is within the range of about 0.5 weight percent to about 6 weight percent, and will preferably be include at a level which is within the range of about 1 weight percent to about 5 weight percent. The palmitoyl pentapeptide will more preferably be included at a level which is within the range of 2 weight percent to 4 weight percent.

It can be desirable to include other naturally occurring antioxidants in the skin cream compositions of this invention. For instance, the extract of the subripe berry of the plant Coffea arabica, from which the ripened and roasted coffee bean is also derived, can beneficially be utilized in the skin cream compositions of this invention. This extract is rich in natural polyphenolic antioxidants including condensed proanthocyanidins and chlorogenic, quinic, and ferulic acids. These polyphenolic antioxidants can be used in the skin cream individually or in various combinations to protect skin from free radical oxidative attack.

Skin cream formulations that are comprised of extracts of subripe berries of Coffea Arabica plants, at least one alkyl lactate, and a base cream can also be made in accordance with this invention. Such skin cream formulations will typically contain (1) a polyphenolic antioxidant selected from the group consisting of condensed proanthocyanidins, chlorogenic acid, quinic acid, and ferulic acid; (2) at least one an alkyl lactate, and (3) a base cream (a pharmaceutically acceptable carrier). It is typically preferred for a combination of ethyl lactate and isoamyl lactate to be used in such compositions. The total level of polyphenolic antioxidants present in such skin cream formulations will typically be within the range of 0.01 weight percent to 2 weight percent, based upon the total weight of the skin cream formulation. Skin cream formulations of this type will more typically contain from about 0.05 weight percent to about 1 weight percent polyphenolic antioxidants, based upon the total weight of the skin cream formulation.

In making the skin cream formulations of this invention the ascorbic acid, the zinc salt, the amino acid, the optional carnosic acid, the optional palmitoyl pentapeptide, the optional idebenone, and additional desired materials are mixed into a pharmaceutically acceptable carrier, such as a base cream. Pharmaceutically acceptable carriers are described in U.S. Pat. No. 7,022,317 and can be in any presentation form normally used in cosmetics or dermatology, and it may especially be in the form of an optionally gelled aqueous solution, a dispersion of the lotion type, optionally a two-phase lotion, an emulsion obtained by dispersing a fatty phase in an aqueous phase (oil/water emulsion) or conversely (water/oil emulsion), or a triple emulsion (water/oil/water or oil/water/oil emulsion) or a vesicular dispersion of ionic and/or nonionic type. These compositions are prepared according to usual methods. A composition in the form of an oil-in-water emulsion is preferably used according to this invention.

This composition may be more or less fluid and may have the appearance of a white or colored cream, an ointment, a milk, a lotion, a serum, a paste or a mousse. It may optionally be applied in the form of an aerosol. It may also be in solid form, in particular in the form of a stick. It may be used as a care product, and/or as a makeup product for the skin.

In a known manner, the composition used according to the invention may also contain adjuvants that are common in cosmetics, such as hydrophilic or lipophilic gelling agents, hydrophilic or lipophilic active agents, preserving agents, antioxidants, solvents, fragrances, fillers, UV-screening agents, pigments, odor absorbers and dyestuffs. The amounts of these various adjuvants are those conventionally used in the field under consideration, and, for example, from 0.01% to 20% relative to the total weight of the composition. Depending on their nature, these adjuvants may be introduced into the fatty phase, into the aqueous phase, or into lipid vesicles.

When the composition used according to the invention is an emulsion, the proportion of the fatty phase may range from 5% to 80% by weight and preferably from 5% to 50% by weight relative to the total weight of the composition. The oils, emulsifiers and co-emulsifiers used in the composition in emulsion form are chosen from those conventionally used in the field under consideration. The emulsifier and co-emulsifier are present in the composition in a proportion ranging from 0.3% to 30% by weight and preferably from 0.5% to 20% by weight relative to the total weight of the composition.

As oils that may be used in the invention, mention may be made of mineral oils (liquid petroleum jelly), oils of plant origin (avocado oil or soybean oil), oils of animal origin (lanolin), synthetic oils (perhydrosqualene), silicone oils (cyclomethicone) and fluoro oils (perfluoropolyethers). Fatty alcohols (cetyl alcohol), fatty acids and waxes (carnauba wax or ozokerite) may also be used as fatty substances.

As examples of emulsifiers and co-emulsifiers that may be used in the invention, mention may be made of fatty acid esters of polyethylene glycol such as PEG-100 stearate, and fatty acid esters of glycerol such as glyceryl stearate, or mixtures thereof.

Hydrophilic gelling agents that may be mentioned in particular include carboxyvinyl polymers (carbomer), acrylic copolymers such as acrylate/alkylacrylate copolymers, polyacrylamides, polysaccharides, natural gums and clays, and lipophilic gelling agents that may be mentioned include modified clays, for instance bentones, metal salts of fatty acids, hydrophobic silica and polyethylenes.

Dermabase cream, Unibase cream, and Vanicream are representative examples of commercially available base creams that can be used as the pharmaceutically acceptable carrier in the practice of this invention.

The topical formulations of this invention can also contain: (1) moisturizers, (2) depigmenting or propigmenting agents, (3) antimicrobial agents, (4) anti-pollution agents or free-radical scavengers, (5) NO-synthase inhibitors, (6) agents for stimulating the synthesis of dermal or epidermal macromolecules and/or for preventing their degradation, (7) agents for stimulating the proliferation of fibroblasts or keratinocytes and/or keratinocyte differentiation, (8) dermo-decontracting agents, (9) tensioning agents, (10) calmatives, (11) agents acting on the capillary circulation, and (12) agents acting on the energy metabolism of cells. Examples of these additional materials that can be included in the skin cream formulations of this invention include:

1. Moisturizers

The moisturizers that can be used in the skin cream formulations of this invention either act on the barrier function of the skin or as an occlusive compound. Mention may be made of ceramides, sphingoid-based compounds, lecithins, glycosphingolipids, phospholipids, cholesterol and its derivatives, phytosterols (stigmasterol, β-sitosterol or campesterol), essential fatty acids, 1,2-diacylglycerol, 4-chromanone, pentacyclic triterpenes such as ursolic acid, petroleum jelly and lanolin; or a compound that directly increases the water content of the stratum corneum, such as threalose and its derivatives, hyaluronic acid and its derivatives, glycerol, pentanediol, sodium pidolate, serine, xylitol, sodium lactate, polyglyceryl acrylate, ectoin and its derivatives, chitosan, oligosaccharides and polysaccharides, cyclic carbonates, N-lauroylpyrrolidonecarboxylic acid and N-α-benzoyl-L-arginine; or a compound that activates the sebaceous glands, such as steroid derivatives (such as DHEA, its 7-oxide and 17-alkyl derivatives and sapogenins) and vitamin D and its derivatives. These compounds may represent from 0.001% to 30% and preferably from 0.01% to 20% relative to the total weight of the composition according to the invention. The composition according to the present invention comprising the moisturizers mentioned above is advantageously intended for preventing or treating dryness of the skin and especially xerosis.

2. Depigmenting or Propigmenting Agent

The depigmenting agents that may be incorporated into the composition according to the present invention comprise, for example, the following compounds: kojic acid; ellagic acid; arbutin and its derivatives such as those described in patent applications EP-895 779 and EP-524 109; hydroquinone; aminophenol derivatives such as those described in patent applications WO 99/10318 and WO 99/32077, and in particular N-cholesteryloxycarbonyl-para-aminophenol and N-ethyloxycarbonyl-para-aminophenol; iminophenol derivatives, in particular those described in patent application WO 99/22707; L-2-oxothiazolidine-4-carboxylic acid or procysteine, and also its salts and esters; ascorbic acid and its derivatives, especially ascorbyl glucoside; and plant extracts, in particular extracts of liquorice, of mulberry and of skullcap, without this list being limiting.

Propigmenting agents that may be mentioned include the extract of burnet (*Sanguisorba officinalis*) sold by the company Maruzen, and extracts of chrysanthemum (*Chrysanthemum morifolium*). The composition according to the present invention comprising the depigmenting agents mentioned above is advantageously intended for preventing or treating hyperpigmentation, in particular pigmentation marks associated with ageing of the skin. For its part, the composition containing the propigmenting agents mentioned above is preferably intended for treating baldness.

3. Antimicrobial Agents

The antimicrobial agents that may be used in the composition according to the invention may be chosen especially from 2,4,4'-trichloro-2'-hydroxydiphenyl ether (or triclosan), 3,4,4'-trichlorobanilide, phenoxyethanol, phenoxypropanol, phenoxyisopropanol, hexamidine isethionate, metronidazole and its salts, miconazole and its salts, itraconazole, terconazole, econazole, ketoconazole, saperconazole, fluconazole, clotrimazole, butoconazole, oxiconazole, sulfaconazole, sulconazole, terbinafine, ciclopirox, ciclopiroxolamine, undecylenic acid and its salts, benzoyl peroxide, 3-hydroxybenzoic acid, 4-hydroxybenzoic acid, phytic acid, N-acetyl-L-cysteine acid, lipoic acid, azelaic acid and its salts, arachidonic acid, resorcinol, 2,4,4'-trichloro-2'-hydroxydiphenyl ether, 3,4,4'-trichlorocarbanilide, octopirox, octoxyglycerine, octanoylglycine, caprylyl glycol, 10-hydroxy-2-decanoic acid, dichlorophenyl imidazole dioxolane and its derivatives, described in patent WO 93/18743, farnesol and phytosphingosines, and mixtures thereof. The preferred antibacterial agents are triclosan, phenoxyethanol, octoxyglycerine, octanoylglycine, 10-hydroxy-2-decanoic acid, caprylyl glycol, farnesol and azelaic acid. By way of example, the antimicrobial agent may be used in the composition according to the invention in an amount representing from 0.1% to 20% and preferably from 0.1% to 10% relative to the total weight of the composition. The composition containing the antimicrobial agent is particularly suitable for use in treating acne-prone greasy skin, acne or scalp dandruff.

4. Anti-Pollution Agent or Free-Radical Scavenger

The term "anti-pollution agent" means any compound capable of trapping ozone, monocyclic or polycyclic aromatic compounds such as benzopyrene and/or heavy metals such as cobalt, mercury, cadmium and/or nickel. The term "free-radical scavenger" means any compound capable of trapping free radicals. As ozone-trapping agents that may be used in the composition according to the invention, mention may be made in particular of vitamin C and its derivatives including ascorbyl glucoside; phenols and polyphenols, in particular tannins, ellagic acid and tannic acid; epigallocatechin and natural extracts containing it; extracts of olive tree leaf; extracts of tea, in particular of green tea; anthocyans; extracts of rosemary; phenol acids, in particular chlorogenic acid; stilbenes, in particular resveratrol; sulphur-containing amino acid derivatives, in particular S-carboxymethylcysteine; ergothioneine; N-acetylcysteine; chelating agents, for instance N,N'-bis(3,4,5-trimethoxybenzyl)ethylenediamine or one of its salts, metal complexes or esters; carotenoids such as crocetin; and various starting materials, for instance the mixture of arginine, histidine ribonucleate, mannitol, adenosine triphosphate, pyridoxine, phenylalanine, tyrosine and hydrolysed RNA, sold by the Laboratoires Serobiologiques under the trade name CPP LS 2633-12F®, the water-soluble fraction of corn sold by the company Solabia under the trade name Phytovityl®, the mixture of extract of fumitory and of extract of lemon sold under the name Unicotrozon C-49® by the company Induchem, and the mixture of extracts of ginseng, of apple, of peach, of wheat and of barley, sold by the company Provital under the trade name Pronalen Bioprotect®.

As agents for trapping monocyclic or polycyclic aromatic compounds, which may be used in the composition according to the invention, mention may be made in particular of tannins such as ellagic acid; indole derivatives, in particular 3-indolecarbinol; extracts of tea, in particular of green tea, extracts of water hyacinth or *Eichhornia crassipes*; and the water-soluble fraction of corn sold by the company Solabia under the trade name Phytovityl®.

Finally, as heavy-metal-trapping agents that may be used in the composition according to the invention, mention may be made in particular of chelating agents such as EDTA, the pentasodium salt of ethylenediaminetetra-methylenephosphonic acid, and N,N'-bis(3,4,5-trimethoxybenzyl)ethylenediamine or one of the salts, metal complexes or esters thereof; phytic acid; chitosan derivatives; extracts of tea, in particular of green tea; tannins such as ellagic acid; sulphur-containing amino acids such as cysteine; extracts of water hyacinth (*Eichhornia crassipes*); and the water-soluble fraction of corn sold by the company Solabia under the trade name Phytovityl®.

The free-radical scavengers that may be used in the composition according to the invention comprise, besides certain anti-pollution agents mentioned above, vitamin E and its derivatives such as tocopheryl acetate; bioflavonoids; coenzyme Q10 or ubiquinone; certain enzymes, for instance catalase, superoxide dismutase, lactoperoxidase, glutathione peroxidase and quinone reductases; glutathione; benzylidenecamphor; benzylcyclanones; substituted naphthalenones; pidolates; phytanetriol; gamma-oryzanol; lignans; and melatonin.

5. NO-Synthase Inhibitor

Examples of NO-synthase inhibitors that are suitable for use in the present invention especially comprise an extract of a plant of the species *Vitis vinifera* which is sold especially by the company Euromed under the name Leucocyanidines de raisins extra, or by the company Indena under the name Leucoselect®, or finally by the company Hansen under the name Extrait de marc de raisin; an extract of a plant of the species *Olea europaea* which is preferably obtained from olive tree leaves and is sold especially by the company Vinyals in the form of a dry extract, or by the company Biologia & Technologia under the trade name Eurol BT; and an extract of a plant of the species *Gingko biloba* which is preferably a dry aqueous extract of this plant sold by the company Beaufour under the trade name *Gingko biloba* extrait standard. The composition according to the invention comprising an NO-synthane inhibitor as defined above can advantageously be used to present or treat signs of ageing of the skin and/or sensitive skin.

6. Agent for Stimulating the Synthesis of Dermal or Epidermal Macromolecules and/or for Preventing their Degradation Among the active agents for stimulating dermal macromolecules or for preventing their degradation, mention may be made of those that act: either on collagen synthesis, such as extracts of *Centella asiatica; asiaticosides* and *derivatives*; ascorbic acid or vitamin C and its derivatives; synthetic peptides such as lamin, biopeptide CL or the palmitoyloligopeptide sold by the company Sederma; peptides extracted from plants, such as the soybean hydrolysate sold by the company Coletica under the trade name Phytokine®; and plant hormones such as auxins and lignans; or on elastin synthesis, such as the extract of *Saccharomyces cerivisiae* sold by the company LSN under the trade name Cytovitin®; and the extract of the alga *Macrocystis pyrifera* sold by the company Secma under the trade name Kelpadelie®; or on glycosaminoglycan synthesis, such as the product of fermentation of milk with *Lactobacillus vulgaris*, sold by the company Brooks under the trade name Biomin Yogourth®; the extract of the brown alga *Padina pavonica* sold by the company Alban Muller under the trade name HSP3; and the extract of *Saccharomyces cerevisiae* available especially from the company Silab under the trade name Firmalift® or from the company LSN under the trade name Cytovitin®; or on fibronectin synthesis, such as the extract of the zooplankton Salina sold by the company Seporga under the trade name GP4G®; the yeast extract available especially from the company Alban Muller under the trade name Drieline®; and the palmitoyl pentapeptide sold by the company Sederma under the trade name Matrixil®; or on the inhibition of metalloproteases (MMPs), such as, more particularly, MMP 1, 2, 3 or 9. Mention may be made of: retinoids and derivatives, oligopeptides and lipopeptides, lipoamino acids, the malt extract sold by the company Coletica under the trade name Collalift®; extracts of blueberry or of rosemary; lycopene; isoflavones, their derivatives or plant extracts containing them, in particular extracts of soybean (sold, for example, by the company Ichimaru Pharcos under the trade name Flavosterone SB®), of red clover, of flax, of kakkon, or of sage; or on the inhibition of serine proteases such as leukocyte elastase or cathepsin G. Mention may be made of: the peptide extract of Leguminosa seeds (*Pisum sativum*) sold by the company LSN under the trade name Parelastyl®; heparinoids; and pseudodipeptides such as {2-[acetyl-(3-trifluoromethylphenyl)amino]-3-methylbutynylamino}acetic acid.

Among the active agents that stimulate epidermal macromolecules, such as fillagrin and keratins, mention may be made especially of the extract of lupin sold by the company Silab under the trade name Structurine®; the extract of beech *Fagus sylvatica* buds sold by the company Gattefosse under the trade name Gatuline®; and the extract of the zooplankton Salina sold by the company Seporga under the trade name GP4G®.

The composition according to the invention containing one or more of the above compounds is particularly suitable for use in preventing or treating signs of ageing of the skin, in particular of loss of firmness and/or of elasticity of the skin.

7. Agent for Stimulating the Proliferation of Fibroblasts or Keratinocytes and/or Keratinocyte Differentiation The agents for stimulating the proliferation of fibroblasts that may be used in the composition according to the invention may be chosen, for example, from plant proteins or polypeptides, extracts, especially of soybean (for example an extract of soybean sold by the company LSN under the name Eleseryl SH-VEG 8 or sold by the company Silab under the trade name Raffermine®); and plant hormones such as gibelrellins and cytokinins.

The agents for stimulating the proliferation of keratinocytes that may be used in the composition according to the invention especially comprise retinoids such as retinol and its esters, including retinyl palmitate; phloroglucinol; extracts of nut cakes sold by the company Gattefosse; and extracts of Solanum tuberosum sold by the company Sederma.

The agents for stimulating keratinocyte differentiation comprise, for example, minerals such as calcium; the extract of lupin sold by the company Silab under the trade name Photopreventine®; sodium beta-sitosteryl sulphate sold by the company Seporga under the trade name Phytocohesine®; and the extract of corn sold by the company Solabia under the trade name Phytovityl®; and lignans such as secoisolariciresinol. The composition according to the invention comprising these compounds is preferably intended to be used for preventing or treating signs of ageing of the skin.

8. Dermo-Decontracting Agent

The dermo-decontracting agents that may be used in the composition according to the invention comprise alverine and its salts, manganese gluconate, Diazepam, the hexapeptide argireline R sold by the company Lipotec, certain carbonylated secondary and tertiary amines, adenosine, and also sapogenins and the natural extracts, in particular of Wild Yam, containing them. The composition according to the invention comprising these compounds is preferably intended to be used for preventing or treating signs of ageing of the skin, and in particular wrinkles.

9. Tensioning Agent

The term "tensioning agent" means a compound capable of exerting tension on the skin, the effect of which is to temporarily fade out irregularities on the skin's surface, such as wrinkles, and fine lines. Among the tensioning agents that may be used in the composition according to the present invention, mention may be made especially of: (1) synthetic polymers, such as polyurethane latices or acrylic-silicone latices, in particular those described in patent application EP-1 038 519, such as a propylthio(polymethyl acrylate), propylthio(polymethyl methacrylate) and propylthio(polymethacrylic acid) grafted polydimethylsiloxane, or alternatively a propylthio(polyisobutyl methacrylate) and propylthio (polymethacrylic acid) grafted polydimethylsiloxane. Such grafted silicone polymers are sold especially by the company 3M under the trade names VS 80, VS 70 or LO21 (2) polymers of natural origin, especially (a) polyholosides, for example (i) in the form of starch derived especially from rice, corn, potato, cassaya, pea, *Triticum aestivum* wheat, oat, etc. or (ii) in the form of carrageenans, alginates, agars, gelans, cellulose-based polymers and pectins, advantageously as an aqueous dispersion of gel microparticles, and (b) latices consisting of shellac resin, sandarac gum, dammar resins, elemi gums, copal resins and cellulose-based derivatives, and mixtures thereof, (3) plant proteins and protein hydrolysates, in particular from corn, rye, *Triticum aestivum* wheat, buckwheat, sesame, spelt, pea, bean, lentil, soybean and lupin, (4) mixed silicates, especially phyllosilicates and in particular Laponites, (5) wax microparticles chosen, for example, from carnauba wax, candelilla wax and alfalfa wax, (6) colloidal particles of mineral filler with a number-average diameter of between 0.1 and 100 nm and preferably between 3 and 30 nm, chosen, for example, fiom: silica, silic-alumina composites, cerium oxide, zirconium oxide, alumina, calcium carbonate, barium sulphate, calcium sulphate, zinc oxide and titanium dioxide. The compositions according to the invention comprising the above tensioning agents are advantageously intended for treating signs of ageing of the skin, in particular wrinkles and fine lines.

10. Calmatives

As calmatives that may be used in the composition according to the invention, mention may be made of: pentacyclic triterpenes and extracts of plants (e.g.: *Glycyrrhiza glabra*) containing them, for instance .beta.-glycyrrhetinic acid and salts and/or derivatives thereof (glycyrrhetinic acid monoglucoronide, stearyl glycyrrhetinate or 3-stearoyloxyglycyrrhetic acid), ursolic acid and its salts, oleanolic acid and its salts, betulinic acid and its salts, an extract of *Paeonia suffruticosa* and/or *lactiflora*, salicylic acid salts and in particular zinc salicylate, the phycosaccharides from the company Codif, an extract of *Laminaria saccharina*, canola oil, bisabolol and camomile extracts, allantoin, Sepivital EPC (phosphoric diester of vitamins E and C) from SEPPIC, omega-3 unsaturated oils such as musk rose oil, blackcurrant oil, ecchium oil, fish oil, plankton extracts, capryloylglycine, Seppicalm VG (sodium palmitoylproline and *Nymphea alba*) from SEPPIC, an extract of Pygeum, an extract of *Boswellia serrata*, an extract of *Centipeda cunnighami*, an extract of *Helianthus annuus*, an extract of *Linum usitatissimum, tocotrienols*, extracts of *Cola nitida*, piperonal, an extract of clove, an extract of *Epilobium angustifolium, Aloe vera*, an extract of *Bacopa moniera*, phytosterols, cortisone, hydrocortisone, indomethacin and betamethasone.

11. Agents Acting on the Capillary Circulation

The active agents acting on the capillary circulation (vasoprotective or vasodilating agents) may be chosen from flavonoids, ruscogenins, esculosides, escin extracted from common horse chestnut, nicotinates, heperidine methyl chalcone, essential oils of lavender or of rosemary, and extracts of *Ammi visnaga*. The amount of these active agents may vary within a wide range. In general, these active agents are present in a concentration ranging from 0.01% to 15% and preferably from 0.05% to 10% by weight relative to the total weight of the composition.

12. Agents Acting on the Energy Metabolism of Cells

The active agents concerned are those acting on the energy metabolism of the skin, for instance, and in a non-limiting manner, ATP synthesis, and also those involved in the respiratory chain of the cell or in the energy reserves. Mention may be made of coenzyme Q10 (ubiquinone), cytochrome C, creatine or phosphocreatine.

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLE 1

In this experiment a topical skin cream was made utilizing Vanicream™ skin cream as the base cream. Vanicream™ skin cream is a non-greasy, non-comedogenic oil-in-water emulsion that consists of purified water, white petrolatum, cetearyl alcohol and ceteareth-20, sorbitol solution, propylene glycol, simethicone, glyceryl monostearate, polyethylene glycol monostearate, sorbic acid, and butylated hydroxytoluene (BHT). In the procedure used 1 g (gram) of ascorbic acid, 500 mg (milligrams) of zinc sulfate, 200 mg of idebenone, and 500 mg of phenylalanine were mixed into 10 grams of the Vanicream™ base cream. Then, the liquid components (1.5 g of α-tocopherol, 100 mg of ethyl lactate, and 50 mg of rosemary extract) were mixed into the formulation.

The topical skin cream formulation made was soothing when applied to dry skin and had good moisturizing characteristics. It also provided a nice warm glow to skin onto which it was applied. This skin cream formulation had a slight odor, but was not obnoxious. It did not yellow after being stored at room temperature for three weeks.

EXAMPLE 2

In this experiment a topical skin cream was made using the procedure described in Example 1 except one drop of mango oil was added to the formulation with the liquid components. The topical skin cream formulation made was soothing when applied to dry skin and had good moisturizing characteristics. It also provided a nice warm glow to skin onto which it was applied. This skin cream formulation had a very pleasant mango fragrance. In fact, the odor of the ethyl lactate was completely masked. It did not yellow after being stored at room temperature for three weeks.

EXAMPLE 3

In this experiment a topical skin cream was made using the procedure described in Example 1 except that α-tocopherol was not included in the formulation. The topical skin cream formulation made was soothing when applied to dry skin and had good moisturizing characteristics. This skin cream formulation had a strong odor which was deemed to be obnoxious. This skin cream formulation yellowed significantly after being stored at room temperature for three weeks

EXAMPLE 4

In this experiment a topical skin cream was made using the procedure described in Example 1 except that the level of α-tocopherol was reduced to 500 mg. The topical skin cream formulation made was soothing when applied to dry skin and had good moisturizing characteristics. This skin cream formulation had a slight odor, but was not obnoxious. However, this skin cream formulation yellowed after being stored at room temperature for three weeks

EXAMPLE 5

In this experiment a topical skin cream was made using the procedure described in Example 1 except that the level of α-tocopherol was increased to 3 grams. The topical skin cream formulation made was soothing when applied to dry skin and had good moisturizing characteristics. It also provided a nice warm glow to skin onto which it was applied. This skin cream formulation had a slight odor, but was not obnoxious. However, this skin cream formulation yellowed significantly after being stored at room temperature for three weeks

EXAMPLE 6

In this experiment a topical skin cream was made using the procedure described in Example 1 except that 35 mg of isoamyl lactate was added to the formulation with the liquid components. The topical skin cream formulation made was soothing when applied to dry skin and had good moisturizing characteristics. This skin cream formulation had a slight odor, but was not obnoxious.

EXAMPLE 7

In this experiment a topical skin cream was made using the procedure described in Example 6 except that one drop of mango oil was added to the formulation with the liquid components. The topical skin cream formulation made was soothing when applied to dry skin and had good moisturizing characteristics. It also provided a nice warm glow to skin onto which it was applied. This skin cream formulation had a very pleasant mango fragrance. In fact, the odor of the ethyl lactate was completely masked.

EXAMPLE 8

In this experiment a topical skin cream was made using the procedure described in Example 1 except that tyrosine was substituted for the phenylalanine. The topical skin cream formulation made was soothing when applied to dry skin and had good moisturizing characteristics. It also provided a nice warm glow to skin onto which it was applied. This skin cream formulation had a slight odor, but was not obnoxious. It did not yellow after being stored at room temperature for three weeks.

EXAMPLE 9

In this experiment a topical skin cream was made using the procedure described in Example 8 except one drop of mango oil was added to the formulation with the liquid components. The topical skin cream formulation made was soothing when applied to dry skin and had good moisturizing characteristics. It also provided a nice warm glow to skin onto which it was applied. This skin cream formulation had a very pleasant mango fragrance. In fact, the odor of the ethyl lactate was completely masked. It did not yellow after being stored at room temperature for three weeks.

EXAMPLE 10

In this experiment a topical skin cream was made utilizing Vanicream™ skin cream as the base cream. In the procedure used 1 g (gram) of ascorbic acid, 500 mg (milligrams) of zinc sulfate, 100 mg of idebenone, and 500 mg of phenylalanine were mixed into 10 grams of the Vanicream™ base cream. Then, the liquid components (1.5 g of α-tocopherol, 70 mg of ethyl lactate, 30 mg of isoamyl lactate, 50 mg of rosemary extract, and one drop of mango oil) were mixed into the formulation. The formulation was mixed with a stirring rod for about 5 minutes to attain a uniform cream composition.

This skin cream formulation made in this experiment had a very pleasant mango fragrance. The odor of the ethyl lactate was completely masked by the isoamyl lactate and the mango. This skin cream composition was evaluated as a facial cream by three adult females. These female subjects applied this skin cream to their faces in the morning after washing their faces. It was reported to have good moisturizing characteristics and was further reported to provide the facial skin to which it was applied with a warm glow. After the skin cream had been absorbed into the skin (dried) the subjects applied their makeup foundation as usual. All of the subjects reported that their foundation glided on more easily than usual. It was further reported that the skin cream composition made a good base for their foundation and helped to prevent the foundation from encrusting or caking. The subjects reported that their makeup did not dissipate and remained fresh over the course of the day. Accordingly, the subjects reported that the facial cream could conveniently be used in conjunction with makeup. None of the subject found the skin cream of this invention to be irritating and all of the subjects observed a reduction in roughness and dryness of their facial skin. All of the subjects further reported an improvement in the texture, softness, smoothness, tone, clarity, and radiance of their skin within 30 minutes of application.

EXAMPLE 11

One of the female subjects repeated the procedure described in Example 10, except that she applied MD Forté sunscreen to her face after allowing the facial cream of this invention to be absorbed into her skin. She again reported that her foundation makeup glided on more easily than usual. It was again reported that the skin cream composition made a good base for her foundation and helped to prevent it from encrusting or caking. She found that her makeup did not dissipate and remained fresh over the course of the day. She observed a reduction in roughness and dryness of her facial skin and again reported an improvement in the texture, softness, smoothness, tone, clarity, and radiance of her skin within 30 minutes of the application. Accordingly, she reported that the facial cream could conveniently be used as part of a daily regimen that includes the application of sunscreen followed by makeup.

EXAMPLE 12

In this experiment a marjoram extract containing carnosic acid was prepared. In the procedure used a mixture containing one part by weight ethyl lactate, one part by weight isoamyl lactate, and one part by weight distilled water was heated to about 90° C. Then, 4 grams of ground marjoram leaves were mixed into 12 grams of the liquid mixture and agitated for about 10 minutes. At that point, the mixture was filtered through a coffee filter to separate the liquid extract from the remaining solid material, such as leaves and plant matter. The marjoram extract was then used in making skin cream samples in accordance with this invention.

EXAMPLE 13

In this experiment a topical skin cream was made utilizing the marjoram extract made in Example 12. In the procedure used Vanicream™ skin cream was again used as the base cream. In the procedure used 1 g (gram) of ascorbic acid, 500 mg (milligrams) of zinc sulfate, 200 mg of idebenone, and 500 mg of phenylalanine were mixed into 10 grams of the Vanicream™ base cream. Then, 1.5 g of α-tocopherol and 150 mg of the marjoram extract were mixed into the formulation.

The topical skin cream formulation made was soothing when applied to dry skin and had good moisturizing characteristics. It also provided a nice warm glow to skin onto which it was applied. This skin cream formulation had a much more pleasing odor than did the formulation made in Example 1 with ethyl lactate and Rosemary extract. It was determined that the marjoram extract made in Example 12 was characterized by a much less intense odor than was exhibited by the Rosemary extract. In any case the skin cream made did not yellow after being stored at room temperature for three weeks.

EXAMPLE 14

In this experiment a topical skin cream was again made utilizing the marjoram extract made in Example 12. In the procedure used Vanicream™ skin cream was again used as the base cream. In the procedure used 12 g of ascorbic acid, 6 g of zinc sulfate, 1 g of BHT, and 7.5 g of phenylalanine were mixed into 300 grams of the Vanicream™ base cream. Then, 15 g of α-tocopherol, 1 g of the marjoram extract, and 1 g of cucumber melon perfume oil were mixed into the formulation. The skin cream made in this experiment did not yellow after being stored at room temperature for over four months.

This skin cream formulation was then used to treat a male patient suffering from chronic dry skin on his hand. This patient was 58 years old and had suffered from severe dry skin (xerosis) on the palmar of his hand for many years. In fact, this patient's dry skin was so pronounced that it frequently developed painful cracks in the skin (fissures) with bleeding occurring from time to time. Over the years this patient had treated his chronic dry skin condition with a wide variety of moisturizing agents without success. However, the skin cream made in this experiment was very effective in reversing the xerosis after it was applied topically. In fact, the topical application of the skin cream of this invention to this patient's hand eliminated the fissures and bleeding. After a few days of applying the skin cream of this invention his skin was reported to have returned to normal.

EXAMPLE 15

In this experiment a topical skin cream was again made utilizing the marjoram extract made in Example 12. In the procedure used Vanicream™ skin cream was again used as the base cream. In the procedure used 12 g of ascorbic acid, 6 g of zinc sulfate, 1 g of idebenone, 1 g of BHT, and 7.5 g of phenylalanine were mixed into 300 grams of the Vanicream™ base cream. Then, 15 g of α-tocopherol, 1 g of the marjoram extract, and 1 g of honeysuckle perfume oil were mixed into the formulation. The skin cream made in this experiment did not yellow after being stored at room temperature for over four months. It was also reported to exhibit a very pleasant fragrance.

This skin cream formulation was then used to treat a female patient suffering from chronic dry skin on her feet. This patient was 79 years old and suffered from xerosis on her feet. In fact, this patient's dry skin was so pronounced that it frequently developed painful fissures in the skin with bleeding occurring from time to time. Over the years this patient had treated her chronic dry skin condition with a wide variety of moisturizing agents without complete success. However, the topical application of the skin cream made in this experiment was very effective with regard to normalizing this patient's skin. In fact, the topical application of the skin cream of this invention to this patient's feet completely eliminated her problem with xerosis of the feet. After a few days of applying the skin cream of this invention the skin on her feet was reported to have returned to normal.

EXAMPLE 16

In this experiment a topical skin cream was again made utilizing the marjoram extract made in Example 12. In the procedure used Vanicream™ skin cream was again used as the base cream. In the procedure used 12 g of ascorbic acid, 6 g of zinc sulfate, 1 g of idebenone, 1 g of BHT, and 7.5 g of phenylatanine were mixed into 300 grams of the Vanicream™ base cream. Then, 15 g of α-tocopherol, 1 g of the marjoram extract, and 1 g of tangerine perfume oil were mixed into the formulation. The skin cream made in this experiment did not yellow after being stored at room temperature for over four months. It was also reported to have a pleasant fragrance.

This skin cream formulation was then used to treat a female patient suffering from xerosis on both of her elbows. The skin on the elbows of this patient was cracked, peeling and discolored. This patient was 49 years old and had previous treated her asteatotic condition of her elbows with a variety of over-the-counter moisturizing creams. However, the over-the-counter commercial products were not effective in moisturizing this patient's elbows. However, the topical application of the skin cream made in this experiment was very effective with regard to moisturizing the dry skin on this patient's elbows. In fact, the topical application of the skin cream of this invention to this patient's elbows completely eliminated her problem within a few days.

EXAMPLE 17

In this experiment a topical skin cream was again made utilizing the marjoram extract made in Example 12. In the procedure used Vanicream™ skin cream was again used as the base cream. In the procedure used 12 g of ascorbic acid, 6 g of zinc sulfate, 1 g of idebenone, 1 g of BHT, and 7.5 g of phenylalanine were mixed into 300 grams of the Vanicream™ base cream. Then, 15 g of α-tocopherol, 1 g of the marjoram extract, and 1 g of mango perfume oil were mixed into the formulation. The skin cream made in this experiment did not yellow after being stored at room temperature for over four months. It was also reported to have a pleasant fragrance.

The facial skin of a 49 year old female patient was evaluated utilizing a Visia Complexion Analysis and Statistical Modeling Engine version 1.2.0 made by Canfield Imaging Systems to establish a base line with respect to spots, pores, wrinkles, and texture. After being evaluated, this patient applied the skin cream made in this experiment to her face both in the morning and evening every day. After approximately four months the facial skin of this patient was re-evaluated after using this cream on a daily basis. This analysis showed a 3% reduction in spots, a 29% reduction in pores, a 29% reduction in wrinkles and a 26% improvement in skin texture. This patient was elated with the overall improvement in the appearance of her skin and was particularly delighted with the perceived reduction in pore size.

EXAMPLE 18

In this experiment a topical skin cream was again made utilizing the marjoram extract made in Example 12. In the procedure used Vanicream™ skin cream was again used as the base cream. In the procedure used 12 g of ascorbic acid, 6 g of zinc sulfate, 1 g of idebenone, 1 g of BHT, and 7.5 g of phenylalanine were mixed into 300 grams of the Vanicream™ base cream. Then, 15 g of α-tocopherol, 1 g of the marjoram extract, and 1 g of mango perfume oil were mixed into the formulation. The skin cream made in this experiment did not yellow after being stored at room temperature for over four months. It was also reported to have a pleasant fragrance.

The facial skin of a 49 year old female patient was evaluated utilizing a Visia Complexion Analysis and Statistical Modeling Engine version 1.2.0 made by Canfield Imaging Systems to establish a base line with respect to spots, pores, wrinkles, and texture. After being evaluated, this patient applied the skin cream made in this experiment to her face both in the morning and evening every day. After approximately four months the facial skin of this patient was re-evaluated after using this cream on a daily basis. This analysis showed a 38% reduction in spots, a 58% reduction in pores, a 40% reduction in wrinkles and a 54% improvement in skin texture. This patient was elated with the dramatic improvement in the appearance of her skin.

While certain representative embodiments and details have been shown for the purpose of illustrating the subject invention, it will be apparent to those skilled in this art that various changes and modifications can be made therein without departing from the scope of the subject invention.

What is claimed is:

1. A topical formulation comprising about 1 weight percent to about 20 weight percent ascorbic acid, about 1 weight percent to about 10 weight percent of phenylalanine, about 0.5 weight percent to about 5 weight percent of a non-toxic zinc salt, a marjoram extract containing carnosic acid, about 1 weight percent to about 30 weight percent α-tocopherol, and about 0.01 weight percent to about 20 weight percent of a mixture of ethyl lactate and isoamyl lactate, wherein the weight ratio of ethyl lactate to isoamyl lactate is within the range of about 1:10 to about 20:1, and a pharmaceutically acceptable carrier.

2. A topical formulation as specified in claim 1 wherein the mixture of ethyl lactate and isoamyl lactate contains from about 30 weight percent to about 70 weight percent ethyl lactate and from about 30 weight percent to about 70 weight percent isoamyl lactate.

3. A topical formulation as specified in claim 1 wherein the mixture of ethyl lactate and isoamyl lactate contains from about 40 weight percent to about 60 weight percent ethyl lactate and from about 40 weight percent to about 60 weight percent isoamyl lactate.

4. A topical formulation as specified in claim 1 wherein the α-tocopherol is present at a level which is within the range of about 2 weight percent to about 8 weight percent.

5. A topical formulation as specified in claim 1 wherein the α-tocopherol is present at a level which is within the range of about 3 weight percent to about 5 weight percent.

6. A topical formulation as specified in claim 1 wherein the carnosic acid is present at a level which is within the range of about 0.01 weight percent to about 1.5 weight percent, based upon the total weight of the topical formulation.

7. A topical formulation as specified in claim 1 which is further comprised of palmitoyl pentapeptide.

8. A topical formulation as specified in claim 1 wherein the mixture of ethyl lactate and isoamyl lactate is present at a level which is within the range of about 0.2 weight percent to about 1 weight percent.

9. A topical formulation as specified in claim 1 wherein the mixture of ethyl lactate and isoamyl lactate is present at a level which is within the range of about 0.2 weight percent to about 0.5 weight percent.

10. A topical formulation as specified in claim 1 wherein the ethyl lactate and the isoamyl lactate are provided to the topical formulation by the marjoram extract which is a liquid system that includes water, ethyl lactate, and isoamyl lactate.

11. A topical formulation as specified in claim 10 wherein the marjoram extract is made by (1) heating a mixture of marjoram leaves in a mixture of water, ethyl lactate, and isoamyl lactate at an elevated temperature which is within the range of about 70° C. to about 100° C. to produce a mixture of the marjoram extract and solid matter, and (2) recovering the marjoram extract from the mixture by filtering out the solid matter.

12. A topical formulation as specified in claim 1 wherein the pharmaceutically acceptable carrier is an oil-in-water emulsion.

13. A topical formulation as specified in claim 12 wherein the oil-in-water emulsion includes white petrolatum.

14. A topical formulation as specified in claim 13 wherein the oil-in-water emulsion is further comprised of cetearyl alcohol, sorbitol, propylene glycol, simethicone, glyceryl monostearate, polyethylene glycol monostearate, and sorbic acid.

* * * * *